United States Patent
Hardten et al.

(10) Patent No.: US 10,206,814 B2
(45) Date of Patent: Feb. 19, 2019

(54) SYSTEM AND METHOD FOR THE DELIVERY OF MEDICATIONS OR FLUIDS TO THE EYE

(71) Applicants: David R. Hardten, Excelsior, MN (US); Richard L. Lindstrom, Wayzata, MN (US)

(72) Inventors: David R. Hardten, Excelsior, MN (US); Richard L. Lindstrom, Wayzata, MN (US)

( * ) Notice: Subject to any disclaimer, the term of this patent is extended or adjusted under 35 U.S.C. 154(b) by 408 days.

(21) Appl. No.: 14/989,072

(22) Filed: Jan. 6, 2016

(65) Prior Publication Data
US 2017/0189229 A1 Jul. 6, 2017

(51) Int. Cl.
*A61F 9/00* (2006.01)

(52) U.S. Cl.
CPC .................. *A61F 9/0017* (2013.01)

(58) Field of Classification Search
CPC .......... A61M 25/0067; A61M 31/00; A61M 31/002; A61M 35/00; A61M 35/003; A61M 35/006; A61M 2210/0612; A61H 35/02; A61F 9/0008; A61F 9/0017
See application file for complete search history.

(56) References Cited

U.S. PATENT DOCUMENTS

| | | | |
|---|---|---|---|
| 3,324,855 A * | 6/1967 | Heimlich | A61B 17/02 401/133 |
| 3,392,725 A * | 7/1968 | Behney | A61D 7/00 351/159.02 |
| 3,485,244 A | 12/1969 | Rosen | |
| 3,519,364 A * | 7/1970 | Truhan | A45D 34/04 401/132 |
| 3,664,340 A | 5/1972 | Morgan | |
| 3,760,807 A | 9/1973 | Neefe | |
| 4,012,798 A | 3/1977 | Liautaud | |
| 4,106,673 A | 8/1978 | Donoghue | |
| 4,484,922 A | 11/1984 | Rosenwald | |
| 4,571,039 A | 2/1986 | Poler | |
| 4,798,599 A | 1/1989 | Thomas | |
| 5,368,590 A | 11/1994 | Itoh | |
| 5,445,462 A * | 8/1995 | Johnson | A61M 35/006 401/132 |

(Continued)

FOREIGN PATENT DOCUMENTS

WO    WO 96/19177    6/1996

*Primary Examiner* — Kami A Bosworth
(74) *Attorney, Agent, or Firm* — Law Offices of Steven W. Weinrieb

(57) ABSTRACT

A method for delivering fluids, drugs, or medications to a patient's eye, and a system or apparatus for implementing the method, is disclosed. The system and method comprises the use of a corneal sponge to be deposited onto the cornea of the patient's eye while the patient's eyelids are maintained in open positions, and a scleral contact lens is disposed onto the sponge. The scleral lens has an irrigation fluid supply tube fluidically connected thereto for supplying a fluid, drug, or medication to the sponge which is saturated with the fluid, drug, or medication. Once the sponge and lens are inserted onto the corneal region of the eye, the patient's eyelids are closed thereby trapping and maintaining the sponge and lens upon the corneal region of the eye so as to permit the fluid, drug, or medication to be continuously supplied and applied to the corneal region of the eye.

10 Claims, 5 Drawing Sheets

(56) References Cited

U.S. PATENT DOCUMENTS

| | | | |
|---|---|---|---|
| 5,556,391 A | 9/1996 | Cercone et al. | |
| 5,618,274 A * | 4/1997 | Rosenthal | A61F 9/0017 |
| | | | 424/427 |
| 6,423,040 B1 | 7/2002 | Benktzon et al. | |
| 7,955,301 B1 * | 6/2011 | McKay | A61M 5/488 |
| | | | 137/517 |
| 2002/0049389 A1 * | 4/2002 | Abreu | A61B 3/1241 |
| | | | 600/558 |
| 2003/0171656 A1 * | 9/2003 | Foulkes | A61B 1/00094 |
| | | | 600/232 |
| 2012/0099077 A1 | 4/2012 | Abt | |
| 2013/0165860 A1 | 6/2013 | Doud et al. | |
| 2014/0121612 A1 | 5/2014 | Rubin et al. | |
| 2014/0249509 A1 * | 9/2014 | Rubinfeld | A61K 9/0048 |
| | | | 604/521 |
| 2014/0316352 A1 * | 10/2014 | Durham | A61M 35/006 |
| | | | 604/290 |
| 2014/0336618 A1 | 11/2014 | Wilkerson et al. | |
| 2016/0199630 A1 * | 7/2016 | Cline | B05B 11/00 |
| | | | 128/200.14 |

* cited by examiner

SYSTEM AND METHOD FOR THE DELIVERY OF MEDICATIONS OR FLUIDS TO THE EYE

FIELD OF THE INVENTION

The present invention relates generally to a system and a method for the delivery of medications or fluids to the eye, and more particularly to a system or method for the delivery of medications or fluids to the eye in connection with corneal collagen crosslinking procedures.

BACKGROUND OF THE INVENTION

Many medical treatment procedures or techniques for treating various different eye conditions comprise processes, techniques, or methods for delivering medications or fluids to the eye in order to, for example, provide drug delivery to the eye or to remove materials or various substances from the eye. In connection with corneal collagen crosslinking procedures or techniques, for example, it is desired to frequently administer riboflavin to the eye. In accordance with such procedures, the riboflavin is typically dropped onto the eye every 1-5 minutes for a period of time extending between 20-30 minutes. Other medications or fluids, which may be utilized for treating other various different ocular conditions, such as, for example, infectious keratitis, which is an inflammation of the cornea caused by bacteria, viruses, fungi, and/or parasites, may comprise various antibiotics or anti-fungal agents. These fluids also often need to be applied to the eye several times within a 30 minute period. Current procedural techniques involve the frequent application of drops to the eye, or the use of high volumes of such fluids to the eye employing various irrigation systems comprising a feeding bottle fluidically connected to a contact lens-like device with, open flow irrigation.

In view of the fact that many of the medications or fluids, that are particularly preferred for use in connection with the treatment of the aforenoted ocular conditions, may be in relatively short supply, and/or may be relatively expensive, it is desirable to retain a predetermined amount of the medication or fluid upon the cornea during the treatment procedure. In addition, because of the labor-intensive nature characteristic of the frequent drop administration procedures, which are necessarily performed by trained medical personnel, such procedures tend to be relatively costly. Accordingly, it would be desirable if procedures, techniques, or methods could be developed, and apparatus or a system for implementing such procedures, techniques, or methods, which would require less frequent human intervention. Furthermore, many of the medication or fluid application procedures require the patient to maintain his or her head in a predetermined position, or to maintain the eyes in a fixed mode, such as, for example, looking straight ahead, or still further, to have their eyelids held open for relatively long periods of time. All of these procedures may result in some level of discomfort to the patient, which is obviously not ideal.

A need therefore exists in the art for a new and improved method, and a system or apparatus for implementing such method, for delivering medications or fluids to the eye that will resolve the aforenoted problems or drawbacks characteristic of the current state of the art and that will achieve the following overall objectives. More particularly, a need exists in the art for a new and improved method, and a system or apparatus for implementing such method, for delivering medications or fluids to the eye which will be cost effective, which will be significantly more comfortable for the patient, and which will enable a sufficient amount of medication or fluid to effectively be constantly or continuously delivered or applied to the eye.

OVERALL OBJECTIVES OF THE INVENTION

The overall objectives of the present invention are to overcome the drawbacks characteristic of, and encountered during, current procedures, techniques, or methods for applying various medications or fluids to a patient's eye, to render a method, technique or procedure for applying medications or fluids to a patient's eye that is significantly more comfortable for the patient being treated, and to enhance the efficiency and effectiveness of the medication or fluid delivery to the patient's eye as well as to constantly retain a predetermined amount of the medication or fluid upon the eye throughout the entire treatment procedure.

SUMMARY OF THE INVENTION

The foregoing and other objectives are achieved in accordance with the teachings and principles of the present invention through the provision of a new and improved method, and a system or apparatus for implementing such method, for delivering medications or fluids to a patient's eye wherein, in accordance with a first embodiment of the method, a scleral contact lens, having an irrigation fluid supply tube attached thereto so as to effectively comprise a contact lens similar to the well-known Morgan lens, as disclosed within U.S. Pat. No. 3,664,340 which issued to Morgan on May 23, 1972, is one of the primary components used in accordance with the techniques or procedures utilized to carry out the method of the present invention. In addition to the scleral contact lens, with the irrigation fluid supply tube attached thereto, a porous corneal sponge, fabricated from a suitable cellulose or similar material, is operatively associated with the scleral contact lens. More particularly, in accordance with the method of the present invention, the eyelids of the eye to be treated are initially held open by means of the fingertips of the doctor or technician performing the treatment method or procedure of the present invention, and a topical anesthesia is applied to the cornea of the eye. The topical anesthesia may comprise any well known anesthesia commonly employed under such conditions such as, for example, tetracaine, proparacaine, lidocaine, or the like. The sponge, containing a small amount of the material or drug to be administered or delivered to the cornea of the eye, is then applied to the surface of the eye and centered over the cornea. The scleral contact lens, with the irrigation fluid supply tube attached thereto, is then effectively placed over the sponge, care being taken to ensure that the sponge and the scleral contact lens are effectively centered upon or mounted or seated directly over the cornea of the eye. In addition, it is important to gently push or depress the scleral contact lens, with its irrigation fluid supply tube attached thereto, onto the sponge such that the sponge is effectively disposed upon the cornea in a trapped state beneath the scleral contact lens. At this point in time, the patient's eyelids can then be closed so as to effectively entrap both the sponge and the lens upon the surface of the eye.

In addition to the foregoing, a syringe, containing the fluid, drug, or medication to be administered to the eye, is operatively connected to the free end of the irrigation fluid supply tube. One of the objectives of the method of the present invention is to provide a relatively low and constant volume of a high concentration of the particular fluid, drug, or medication to be administered or delivered to the eye. Accordingly, a suitable control device is interposed between the syringe and the scleral contact lens so as to in fact control the volume flow and line pressure within the irrigation fluid supply tube. The control device may be, for example, a stopcock type valve, a clamp, or any other suitable means which will limit or control the volume of the fluid flow of the particular fluid, drug, or medication to the corneal sponge and eye to a predetermined degree or volume amount. In accordance with the usage of these components, the plunger of the syringe will then be moved inwardly a predetermined amount so as to cause a relatively small amount of the fluid, drug, or medication to flow through the irrigation fluid supply tube and to effectively saturate the sponge which is disposed over the cornea of the eye. The stopcock or control device is then closed or adjusted, effectively trapping or controlling the flow of the fluid within the system between the stopcock and the sponge. Over time, tears within the patient's eye may tend to dilute the fluid, drug, or medication being delivered to the eye, and accordingly, the stopcock will then be opened or expanded, the plunger of the syringe will be pushed a predetermined amount further inwardly within the syringe whereby an additional amount of the high concentration fluid, drug, or medication will again be delivered to the sponge so as to maintain the same saturated with the fluid, drug, or medication to be delivered to the eye in order to treat the eye, and the stopcock again adjusted. It will be noted that all during this process, the patient is disposed in a reclined position, with his or her eyelids closed, so as to enhance the comfort level of the patient as much as possible.

In accordance with additional or alternative embodiments of the present inventive method, it is to be noted that in lieu of a single irrigation fluid supply tube, a plurality of irrigation fluid supply tubes may be fluidically connected to the scleral lens in an equiangular circumferentially spaced manner so as to ensure the uniform distribution of the fluid, drug, or medication being supplied to the lens and sponge and ultimately to the eye. Furthermore, the scleral lens may effectively be eliminated whereby the irrigation fluid supply tube, or the plurality of irrigation fluid supply tubes, can be fluidically connected directly to the sponge. Still further, in lieu of the scleral lens and the sponge being separate components, they may be integrally affixed together whereby the combined assembly can be disposed over the cornea of the eye.

BRIEF DESCRIPTION OF THE DRAWINGS

Various other features and attendant advantages of the present invention will be more fully appreciated from the following detailed description when considered in connection with the accompanying drawings in which like reference characters designate like or corresponding parts throughout the several views, and wherein.

DETAILED DESCRIPTION OF THE PREFERRED EMBODIMENT

Figure 1:
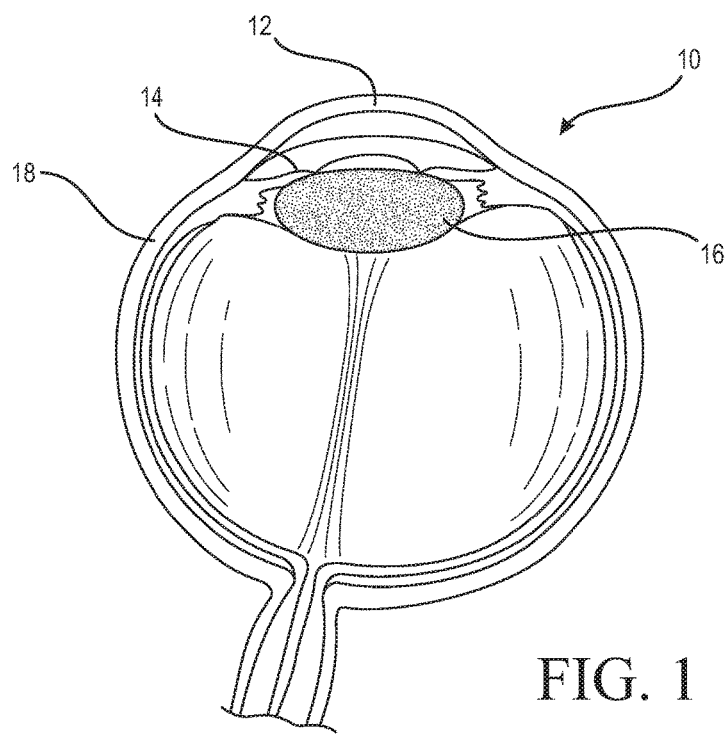
FIG. 1 is a schematic cross-section of the human eye showing, for example, among other components of the eye, the sclera and the cornea.

Referring now to the drawings, and more particularly to FIG. 1, there is initially illustrated a schematic cross-section of the human eye so as to effectively provide background information in order to enhance the understanding of the method of the present invention, and the system or apparatus for implementing such method, for delivering the various fluids, drugs, or medications to the eye. More particularly, it is seen, for example, that the human eye is generally indicated by the reference character 10, and that the eye 10 comprises the cornea 12, which effectively covers, or is disposed in front of, the iris portion 14 of the eye and the lens 16, as well as the sclera 18. As has been noted hereinbefore, the objective of the present invention is to provide a new and improved method, and a new and improved system or apparatus for implementing such method, for delivering fluids, drugs, or medications to the corneal region 12 of the eye.

With reference therefore being made to FIGS. 2-5, the new and improved method, and the system or apparatus for implementing such method, for delivering medications or fluids to a patient's eye 10, is disclosed and is generally indicated by the reference character 100. More particularly, and as can best be seen in FIG. 5, it is seen that in accordance with a first embodiment of the present invention method, and the system or apparatus for implementing the method, a scleral contact lens 102, having an irrigation fluid supply tube 104 attached thereto so as to effectively comprise a contact lens similar to the well-known Morgan lens, is one of the primary components of the system or apparatus 100 of the present invention which is used in accordance with the techniques or procedure utilizled to carry out the method of the present invention in order to safely, comfortably, efficiently, and effectively supply irrigation fluid or medication to the patient's eye 10. It is to be noted, as in the case of the Morgan lens, the outer or external periphery of the scleral contact lens 102 may have a complex cross-sectional configuration in order to effectively accommodate the change in shape and relative steepness characteristic of the cornea 12 with respect to the shape and relative steepness of the sclera 18, as can readily be appreciated from FIG. 1. In addition to the scleral contact lens 102, with the irrigation fluid supply tube 104 attached thereto, a porous corneal sponge 106, which may be fabricated from a suitable cellulose or similar material, is operatively associated with the scleral contact lens 102.

Figure 2:
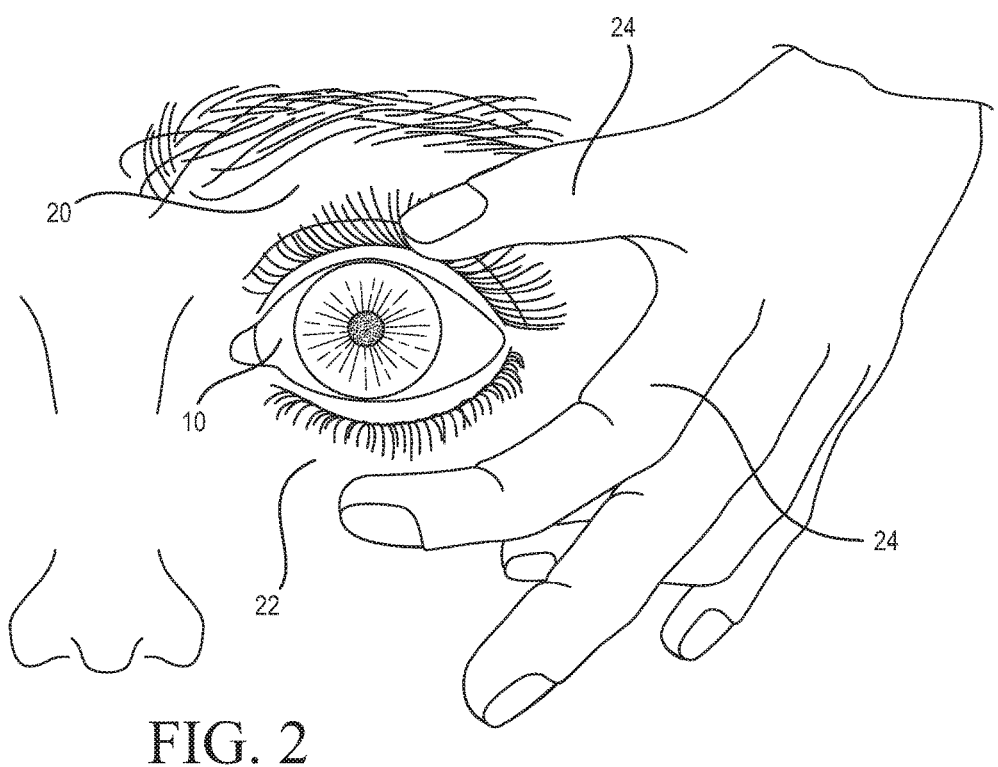
FIG. 2 is a schematic partial front view of a patient's face wherein the first step of the method of the present invention is illustrated as comprising the holding open of the patient's eyelids by means of the fingertips of the doctor or technician who will be performing the method of the present invention.
Figure 3:
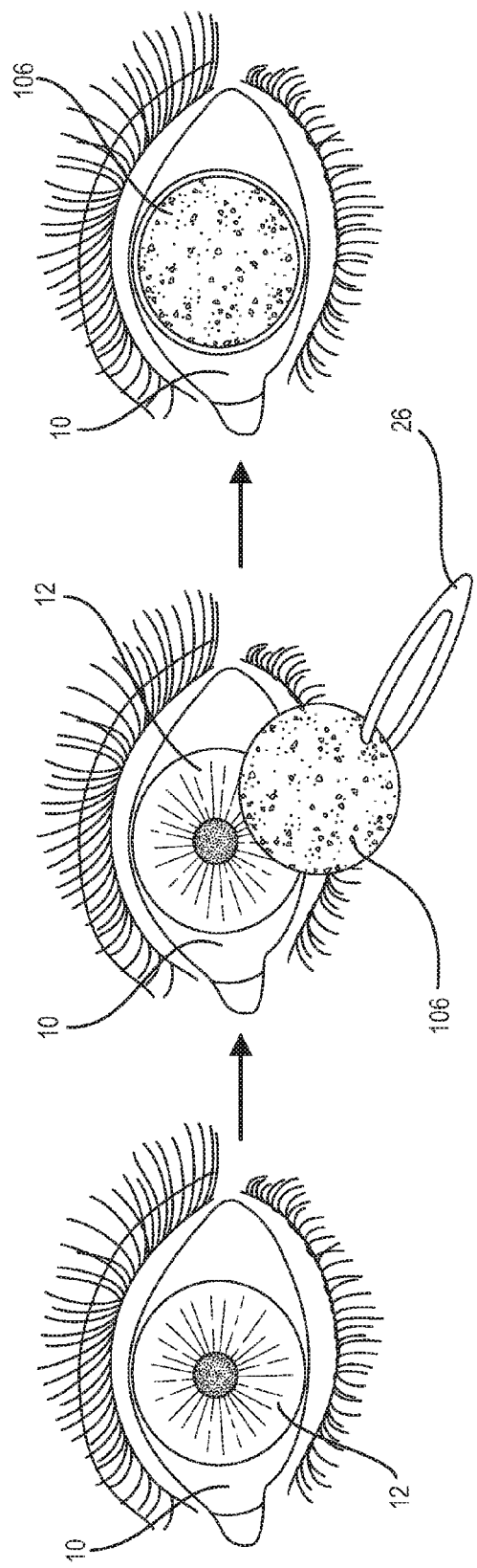
FIGS. 3a,3b,3c are serial schematic views showing the placement of a sponge on the corneal surface of the patient's eye by means of, for example, the use of a forceps, wherein the sponge has had a predetermined amount of the fluid, drug, or medication, to be delivered to the eye in accordance with the method of the present invention, already impregnated therein.
Figure 4:
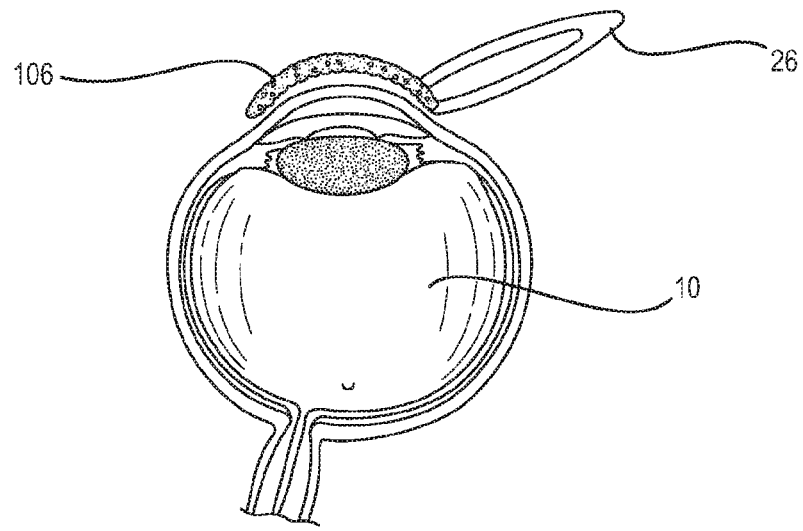
FIG. 4 is a top plan view of the patient's eyeball schematically illustrating the placement of the sponge, in a manner corresponding to that illustrated within FIGS. 3b,3c, upon the patient's eye by means of the forceps.
Figure 5:
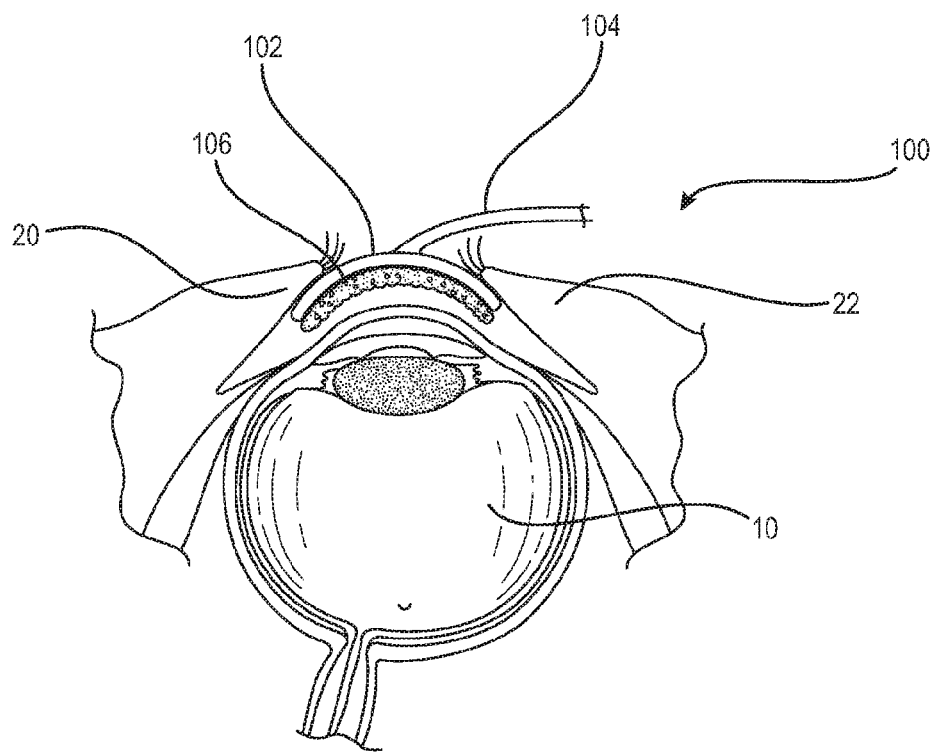
FIG. 5 is a top plan view of the patient's eyeball, similar to that of FIG. 4, showing however the eyelids being moved to their closed position, after the scleral lens, and the irrigation fluid supply tube attached thereto, has been disposed atop the sponge, so as to effectively entrap both the sponge and the scleral lens beneath the eyelids whereby the sponge and scleral lens can effectively be retained in position upon the corneal surface of the eye in preparation for irrigation fluid to be conducted toward and into the sponge.

With reference initially being made to FIG. 2, the method, technique, or procedure of the present invention will begin to be described. In accordance with the present invention method, technique, or procedure, the upper and lower eyelids 20,22 of the patient's eye 10 to be treated are initially held open by means of the fingertips 24 of the doctor or technician performing the treatment method, technique, or procedure of the present invention, and a topical anesthesia is applied to the cornea of the eye. The topical anesthesia may comprise any well known anesthesia commonly employed under such conditions such as, for example, tetracaine, proparacaine, lidocaine, or the like. The sponge 106, containing a small amount of the fluid, drug, or medication to be administered or delivered to the cornea 12 of the eye 10, is then applied to the surface of the eye 10 and centered over the cornea 12 of the eye 10 by using, for example, surgical forceps 26, as can best be seen in FIGS. 3b,3c, and 4. If desired, the sponge 106 can briefly be used to massage the surface of the eye 10 so as to remove any mucous or native tear film that might otherwise slow penetration of the fluid, drug, or medication to be administered or delivered to the cornea 12 of the eye 10. The scleral contact lens 102, with the irrigation fluid supply tube 104 attached thereto, is then effectively placed over the sponge 106, as illustrated within FIG. 5, care being taken to ensure that the sponge 106 and the scleral contact lens 102 are effectively centered upon, or seated or mounted directly over the cornea 12 of the eye 10. In addition, it is important to gently push or depress the scleral contact lens 102, with its irrigation fluid supply tube 104 attached thereto, onto the sponge 106 such that the sponge 106 is effectively disposed upon the cornea 12 of the eye 10 in a trapped state between the surface of the eye 10 and the scleral contact lens 102. At this point in time, the patient's eyelids 20,22 can then be closed so as to, in turn, effectively entrap and retain both the sponge 106 and the lens 102 upon the corneal surface of the eye 10.

Figure 6:
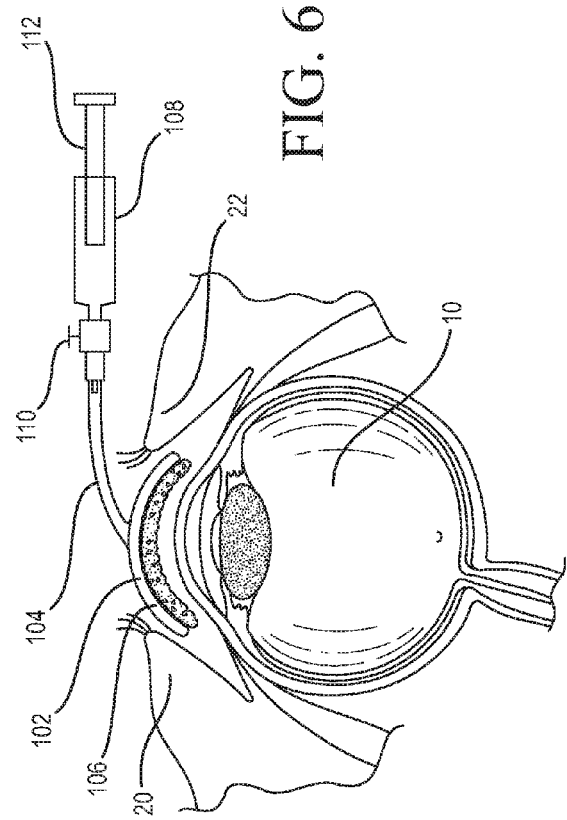
FIG. 6 is a top plan view of the patient's eyeball, similar to that of FIG. 5, additionally showing a fluid injection syringe operatively connected to the free end portion of the irrigation fluid supply tube, and, for example, a stopcock valve operatively associated therewith so as to provide a predetermined volumetric supply and control of the flow of the irrigation fluid, drug, or medication to the corneal sponge.
Figure 7:
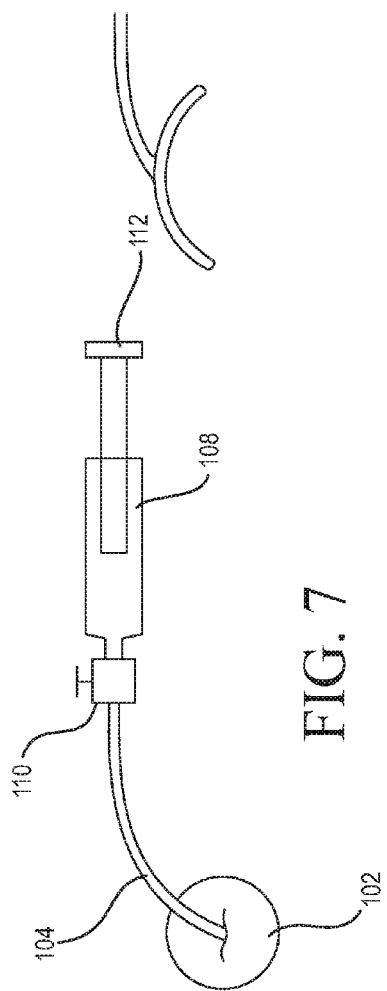
FIG. 7 is an external plan view of a scleral lens having a single irrigation fluid supply tube and syringe/plunger/stopcock assembly operatively connected thereto at, for example, an axially central portion of the scleral lens.

In addition to the foregoing, and with reference being made to FIGS. 6 and 7, a syringe 108, containing the fluid, drug, or medication to be administered or delivered to the eye 10, is operatively connected to the free end of the irrigation fluid supply tube 104. One of the objectives of the method of the present invention is to provide a relatively low and constant volume of a high concentration of the particular fluid, drug, or medication to be administered or delivered to the eye. Accordingly, a suitable control device 110 is interposed between the syringe 108 and the scleral contact lens 102 so as to in fact control the volume flow and line pressure within the irrigation fluid supply tube 104. The control device 110 may be, for example, a stopcock type valve, a clamp, or any other suitable means which will limit or control the volume of the fluid flow of the particular fluid, drug, or medication to the corneal sponge 106 and the eye 10 to a predetermined degree or amount. In accordance with the usage of the noted components, the plunger 112 of the syringe 108 will be moved inwardly a predetermined amount so as to cause a relatively small amount of the fluid, drug or medication to flow through the irrigation tube 104 and to effectively saturate the sponge 106 which is disposed over the cornea 12 of the eye 10. The stopcock or control device 110 is then adjusted, effectively trapping or controlling the flow of the fluid, drug, or medication within the system between the stopcock 110 and the sponge 106. Over time, tears within the patient's eye may tend to dilute the fluid, drug, or medication being delivered to the eye whereupon, in accordance with an additional step of the method of the present invention, the stopcock 110 will be opened or expanded, the plunger 112 of the syringe 108 will be pushed further a predetermined amount into the syringe 108, and an additional amount of the high concentration fluid, drug, or medication will again be delivered to the sponge 106 so as to maintain the same saturated with the fluid, drug or medication being used to treat the eye 10. The stopcock 110 will then be adjusted again so as to control the flow of the fluid, drug, or medication to the desired degree. It will be noted that all during this process or procedure, the patient is disposed in a reclined position, with his or her eyelids closed, so as to enhance the comfort level of the patient as much as possible throughout the entire treatment procedure.

Figure 8:
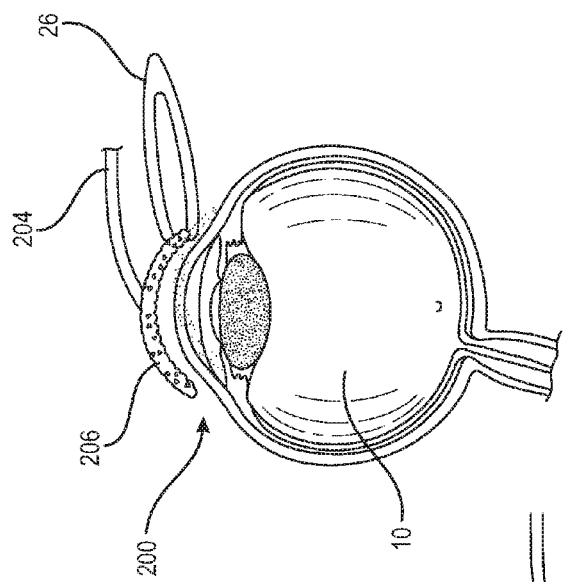
FIG. 8 is a top plan view of the patient's eyeball, similar to that of FIG. 4, schematically illustrating a second embodiment of the present invention wherein the scleral contact lens has effectively been eliminated, and wherein further, the irrigation fluid supply tube is fixedly connected directly to the sponge and the sponge, with the irrigation fluid supply tube connected thereto, is placed upon the patient's eye in a manner corresponding to that illustrated within FIGS. 3b,3c by means of the forceps.

In accordance with additional or alternative embodiments of the present inventive method and the structural components of the system of the present invention for implementing the noted method or procedure, it is to be noted that the scleral lens 102 may effectively be eliminated from the system illustrated, for example, within FIG. 6, whereby the irrigation fluid supply tube 204 would be fluidically connected directly to the sponge 206 by any suitable means, such as, for example, a suitable adhesive or other similar fixation means. This second embodiment of the present invention system is illustrated, for example, within FIG. 8, wherein, in accordance with this second embodiment of the structural system or apparatus 200 of the present invention, component parts have been provided with similar reference characters although they are within the 200 series.

Figure 9:
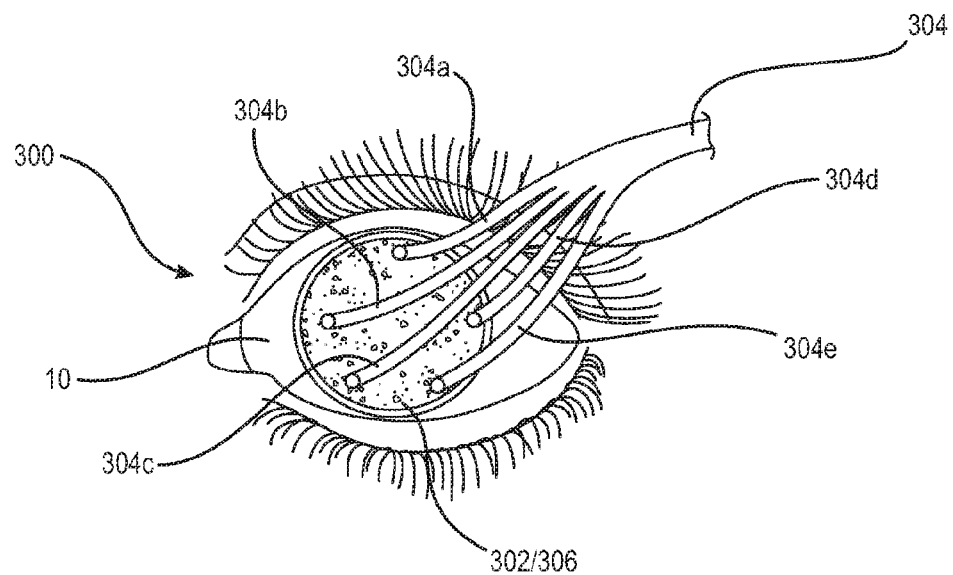
FIG. 9 is an external plan view of a third embodiment of the system of the present invention wherein the scleral lens has a multiplicity of irrigation fluid supply tubes having first end portions thereof connected to the scleral lens while second end portions of the multiplicity of irrigation fluid supply tubes are operatively connected to a single or main irrigation fluid supply tube which is adapted to be operatively connected to a syringe/plunger/stopcock assembly similar to that shown in FIG. 5, whereby the multiplicity of irrigation fluid supply tubes are disposed within an equiangular circumferentially spaced manner around the scleral lens so as to simultaneously provide the fluid, drug, or medication to the underlying sponge at equiangularly spaced locations of the sponge so as to effectively ensure that all regions of the sponge are in fact provided with a predetermined saturation volume of the fluid, drug, or medication to, in turn, be delivered to the cornea of the eye.

Still further, it is also to be noted, as can readily be appreciated from FIGS. 5-8, that the first and second embodiments of the system or apparatus 100,200 of the present invention comprised the use of a single irrigation fluid supply tube 104,204 which was fixedly connected to a central axial portion of the scleral lens 102 or to the central axial portion of the corneal sponge 206. However, as illustrated within FIG. 9, in accordance with the teachings of a third embodiment of the system or apparatus of the present invention, generally indicated by the reference character 300, and in lieu of the use of a single irrigation fluid supply tube 104,204, a plurality of irrigation fluid supply tubes 304a-304e may be integrally connected at first end portions thereof to a main irrigation fluid supply tube 304 and may be fluidically connected at second opposite end portions thereof to the scleral lens 302 or to the corneal sponge 306 so as to ensure the uniform distribution and supply of the fluid, drug, or medication being delivered to the eye. As can readily be seen and appreciated from FIG. 9, the second opposite end portions of the plurality of irrigation fluid supply tubes 304a-304e that are fluidically connected to the scleral lens 302 or to the corneal sponge 306 are fixedly connected to the scleral lens 302 or to the corneal sponge 306 at various locations which are optimally arranged in an equiangular circumferentially spaced manner so as to in fact ensure that the fluid, drug, or medication being delivered or administered to the eye 10 is in fact uniformly distributed to all regions of the corneal sponge so as to, in turn, ensure that all regions of the corneal sponge are uniformly saturated with the fluid, drug, or medication. It is to be noted that while an irrigation fluid supply tube is not illustrated within this embodiment as extending toward and being connected to the axially central portion of the scleral lens 302 or corneal sponge 306, such is in fact to be recognized as an additional possibility in order to ensure the aforenoted objective concerning the equal or uniform distribution of the fluid, drug, or medication to all regions of the scleral lens 302 or corneal sponge 306, such an axially connected irrigation fluid supply tube having been omitted merely for clarity purposes of the drawing figure. It is lastly to be noted that component parts of the third embodiment system 300 that correspond to similar component parts of the first and second embodiment systems 100,200 have been provided with similar reference characters except that they are within the 300 series.

Figure 10:
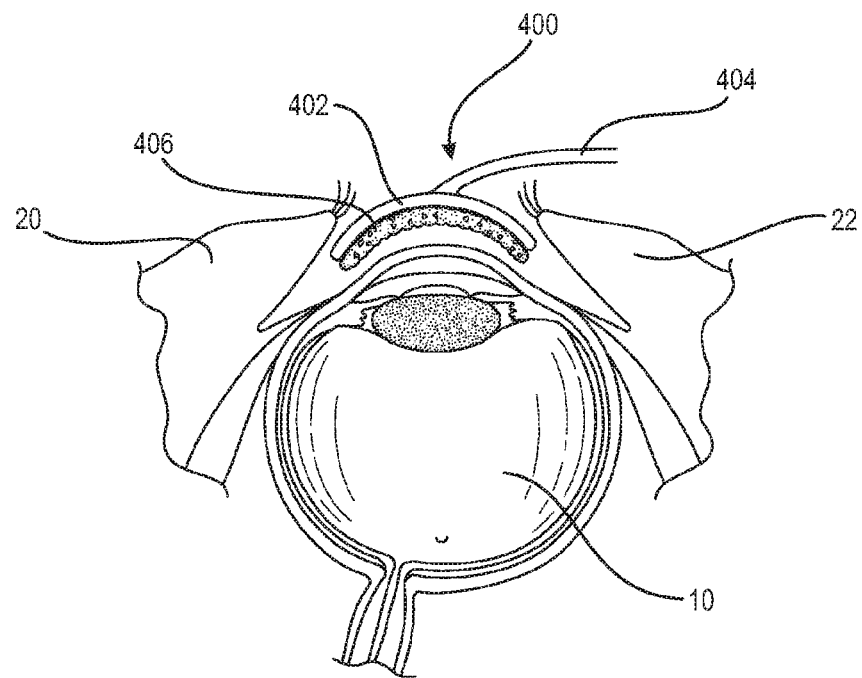
FIG. 10 is a top plan view of the patient's eyeball, similar to that of FIG. 5, showing however the instance wherein the scleral lens and the sponge components comprise an integral one-piece assembly and wherein the eyelids of the patient have been moved to their closed position, after the assembly comprising the scleral lens, the irrigation fluid supply tube attached thereto, and the sponge, have been disposed onto the surface of the eye so as to effectively entrap both the sponge and the scleral lens beneath the eyelids whereby the sponge and scleral lens assembly can effectively be retained in position upon the corneal surface of the eye in preparation for irrigation fluid to be conducted toward and into the sponge and throughout the fluid, drug, or medication application procedure.

Still yet further, as can be readily seen or appreciated from FIG. 10, in lieu of the scleral lens and the corneal sponge comprising separate components that are physically brought into contact with each other, in accordance with a fourth embodiment of the present invention system or apparatus, generally indicated by the reference character 400, the scleral lens 402 and the corneal sponge 404 may be integrally affixed together as a one-piece assembly whereby the combined device can be disposed over the cornea 12 of the eye 10 and then entrapped and retained upon the corneal surface of the eye 10 by means of the closed eyelids 20, 22.

Obviously, many variations and modifications of the present invention are possible in light of the above teachings, and it is to be construed that such variations and modifications are effectively to be included within the claimed method and apparatus. For example, it is to be noted that the corneal sponges may comprise sponges having different thickness dimensions, different sizes, and may be fabricated from different materials comprising different porosity characteristics so as to predetermine saturation volumes and retention times with respect to the fluids, drugs, or medications being delivered to the cornea. The differently-sized corneal sponges can of course be used, for example, depending upon the size of the corneal region being treated. Still further, the corneal sponge can have a diametrical extent which is larger than that of the cornea per se whereby the outer peripheral edge portions of the corneal sponge will effectively be disposed in contact with the sclera, and in this manner, the eyelids will assuredly retain the corneal sponge is contact with the corneal surface of the eye when the patient's eyelids are moved to their closed positions. In a similar manner, the syringes may be characterized by different sizes so as to accommodate various volumes of the fluid, drug, or medication to be delivered. Still yet further, while the system of the present invention has been implemented for the treatment of one eye, the method, technique, or procedure can obviously be repeated for the patient's other eye, or yet alternatively, a bilateral embodiment of the system of the present invention is envisioned such that both eyes of the patient can be treated simultaneously. Yet still further, it is also to be noted that the state of the eye can be such that the epithelium of the cornea is intact, or the epithelium of the cornea has been removed or somehow otherwise altered. After treatment of the particular eye has been completed, the scleral lens and the corneal sponge, or the corneal sponge alone if the scleral lens was omitted from the system and the irrigation fluid supply tube was connected directly to the sponge, is removed from the patient's eye in accordance with a procedure or technique which is effectively the reverse of that described hereinbefore in connection with initial treatment of the patient. It is to be understood that within the scope of the appended claims, the present invention may be practiced otherwise than as specifically described herein.

KEY TO REFERENCE NUMBERS IN THE DRAWINGS

10—EYE
12—CORNEA
14—IRIS
16—LENS
18—SCLERA
20—UPPER EYELID
22—LOWER EYELID
24—FINGERTIPS
26—SURGICAL FORCEPS
100—FIRST EMBODIMENT SYSTEM
102—SCLERAL LENS OF FIRST EMBODIMENT
104—IRRIGATION FLUID SUPPLY TUBE OF FIRST EMBODIMENT
106—CORNEAL SPONGE OF FIRST EMBODIMENT
108—SYRINGE OF FIRST EMBODIMENT
110—CONTROL DEVICE OF FIRST EMBODIMENT
112—PLUNGER OF SYRINGE OF FIRST EMBODIMENT
200—SECOND EMBODIMENT SYSTEM

204—IRRIGATGION FLUID SUPPLY TUBE OF SECOND EMBODIMENT
206—CORNEAL SPONGE OF SECOND EMBODIMENT
300—THIRD EMBODIMENT SYSTEM
302—SCLERAL LENS OF THIRD EMBODIMENT
304—MAIN IRRIGATION FLUID SUPPLY TUBE OF THIRD EMBODIMENT
304a-304e—MULTIPLICITY OF IRRIGATION FLUID SUPPLY TUBES
306—CORNEAL SPONGE OF THIRD EMBODIMENT
400—FOURTH EMBODIMENT SYSTEM
402—SCLERAL LENS OF FOURTH EMBODIMENT
404—IRRIGATION FLUID SUPPLY TUBE OF FOURTH EMBODIMENT
406—CORNEAL SPONGE OF FOURTH EMBODIMENT

What is claimed as new and desired to be protected by Letters Patent of the United States of America, is:

1. A system for delivering a fluid, a drug, or a medication to a corneal region of a human eye so as to treat the corneal region of the human eye with the fluid, the drug, or the medication, comprising:
    a corneal sponge able to be disposed over the corneal region of the human eye, wherein said corneal sponge has a first surface defining a surface area which is substantially the same as the surface area of the corneal region of the human eye, the first surface having a curvature substantially the same as a curvature of the human eye for directly contacting the corneal region of the human eye, and a second surface substantially parallel to the first surface; and
    an irrigation fluid supply tube having a substantially constant outer diameter along its entire length and being connected directly to said second surface of said corneal sponge able to be disposed over the corneal region of the human eye so as to continuously deliver the fluid, the drug, or the medication to said corneal sponge whereby said corneal sponge will be continuously saturated with the fluid, the drug, or the medication such that the corneal region of the human eye is continuously treated with the fluid, the drug, or the medication.

2. The system as set forth in claim 1, wherein:
outer peripheral edge portions of said corneal sponge are able to be disposed beneath the eyelids of the human eye when the eyelids of the human eye are disposed at a closed position whereby the eyelids of the human eye effectively trap said corneal sponge beneath the eyelids of the human eye such that the corneal sponge is maintained in engagement with the corneal region of the human eye.

3. The system as set forth in claim 1, further comprising:
a syringe operatively connected to said irrigation fluid supply tube for forcing a predetermined volume of the fluid, the drug, or the medication through said irrigation fluid supply tube toward said corneal sponge; and
a control device operatively associated with said syringe and interposed between said syringe and said irrigation fluid supply tube for controlling the volumetric amount of the fluid, the drug, or the medication passing through said irrigation fluid supply tube toward said corneal sponge.

4. The system as set forth in claim 1, wherein:
said irrigation fluid supply tube is connected directly to an axially central portion of said corneal sponge.

5. The system as set forth in claim 1, wherein:
said irrigation fluid supply tube comprises multiple irrigation fluid supply tubes connected directly to multiple locations upon said corneal sponge.

6. The system as set forth in claim 5, wherein:
said multiple irrigation fluid supply tubes are disposed within an equiangular circumferential pattern so as to uniformly distribute the fluid, the drug, or the medication to equiangularly spaced regions of said corneal sponge.

7. A method for delivering a fluid, a drug, or a medication to a corneal region of a human eye so as to treat the corneal region of the human eye with the fluid, the drug, or the medication, comprising the steps of:
    disposing a corneal sponge over the corneal region of the human eye, wherein said corneal sponge has a first surface defining a surface area which is substantially the same as the surface area of the corneal region of the human eye, the first surface having a curvature substantially the same as a curvature of the human eye and directly contacting the corneal region of the human eye, and a second surface substantially parallel to the first surface; and
    conducting the fluid, the drug, or the medication through an irrigation fluid supply tube having a substantially constant outer diameter along its entire length and which is connected directly to said second surface of said corneal sponge disposed over the corneal region of the human eye so as to continuously deliver the fluid, the drug, or the medication to said corneal sponge whereby said corneal sponge will be continuously saturated with the fluid, the drug, or the medication such that the corneal region of the human eye is continuously treated with the fluid, the drug, or the medication.

8. A method as set forth in claim 7, further comprising the steps of:
    manipulating the upper and lower eyelids of the human eye to be treated such that the upper and lower eyelids are expanded with respect to each other;
    inserting said corneal sponge, having said irrigation fluid supply tube connected directly thereto, onto the corneal region of the human eye; and
    releasing the upper and lower eyelids of the human eye so as to effectively close the upper and lower eyelids of the human eye such that outer peripheral edge portions of said corneal sponge are able to be disposed beneath the eyelids of the human eye when the eyelids of the human eye are disposed at closed positions whereby the closed eyelids of the human eye effectively trap said corneal sponge beneath the eyelids of the human eye such that the corneal sponge is maintained in engagement with the corneal region of the human eye.

9. The method as set forth in claim 7, wherein said irrigation fluid supply tube comprises multiple irrigation fluid supply tubes and further comprising the steps of:
    connecting first end portions of the multiple irrigation fluid supply tubes to a main irrigation fluid supply tube; and
    connecting second end portions of said multiple irrigation fluid supply tubes directly to multiple locations upon said corneal sponge.

10. The method as set forth in claim 9, comprising the step of:
    disposing said multiple irrigation fluid supply tubes within an equiangular circumferential pattern so as to uniformly distribute the fluid, the drug, or the medication to equiangularly spaced regions of said corneal sponge.

\* \* \* \* \*